United States Patent [19]

Hewett

[11] Patent Number: 5,114,350
[45] Date of Patent: May 19, 1992

[54] CONTROLLED-VOLUME ASSAY APPARATUS

[75] Inventor: Gary E. Hewett, Milpitas, Calif.

[73] Assignee: Cholestech Corporation, Hayward, Calif.

[21] Appl. No.: 320,474

[22] Filed: Mar. 8, 1989

[51] Int. Cl.⁵ .................. C12M 1/34; C12M 1/40; G01N 21/11
[52] U.S. Cl. .................. 435/288; 435/289; 435/291; 435/808; 435/11; 435/25; 435/28; 435/19; 435/15; 422/56; 422/58; 422/82.05; 422/82.09; 422/100; 436/165
[58] Field of Search .......... 422/56, 57, 58, 67, 422/111, 100, 82.05, 82.09; 141/83, 94–95; 436/165; 435/288, 289, 291, 808, 11, 25, 28, 19, 15

[56] References Cited

U.S. PATENT DOCUMENTS

| | | |
|---|---|---|
| 3,508,879 | 4/1970 | Findl et al. ............... 141/94 |
| 3,607,093 | 9/1971 | Stone . |
| 3,791,933 | 2/1974 | Moyer et al. . |
| 3,907,642 | 9/1975 | Richmond . |
| 3,907,645 | 9/1975 | Richmond . |
| 3,925,164 | 12/1975 | Beaucamp et al. . |
| 3,983,005 | 9/1975 | Goodhue et al. . |
| 4,038,485 | 7/1977 | Johnston et al. . |
| 4,069,017 | 1/1978 | Wu et al. . |
| 4,144,129 | 3/1979 | Gruber et al. . |
| 4,144,306 | 3/1979 | Figueras . |
| 4,152,390 | 5/1979 | Nosco et al. ............... 422/58 |
| 4,181,575 | 1/1980 | Gruber et al. . |
| 4,186,251 | 1/1980 | Tarbutton . |
| 4,212,938 | 7/1980 | Gruber et al. . |
| 4,256,693 | 3/1981 | Kondo et al. . |
| 4,399,362 | 8/1983 | Cormier et al. ............ 422/82 |
| 4,435,504 | 3/1984 | Zuk et al. ............... 435/4 |
| 4,477,575 | 10/1984 | Vogel et al. . |
| 4,503,144 | 3/1985 | Deeg et al. . |
| 4,544,630 | 2/1985 | Ziegenhorn et al. . |
| 4,680,259 | 7/1987 | Cumbo et al. . |
| 4,774,192 | 9/1988 | Terminiello et al. ....... 435/14 |
| 4,816,224 | 3/1984 | Vogel et al. . |
| 4,820,489 | 4/1989 | Rothe et al. . |
| 4,826,721 | 5/1989 | Arai et al. . |
| 4,849,340 | 7/1989 | Oberhardt ............... 422/110 |
| 4,877,586 | 10/1989 | Devaney, Jr. et al. ...... 422/58 |
| 4,973,549 | 11/1990 | Khanna et al. ............ 422/61 |

FOREIGN PATENT DOCUMENTS

0229982 12/1985 European Pat. Off. .

Primary Examiner—Jill A. Johnston
Assistant Examiner—Jan M. Ludlow
Attorney, Agent, or Firm—Peter J. Dehlinger; Carol A. Stratford

[57] ABSTRACT

Method and apparatus for use in determining the concentration of a selected analyte in a body-fluid sample. As the fluid sample is applied to a wettable, absorbent reaction pad, the extent of sample wetting of the pad is monitored by surface reflectance. This surface monitoring is used to control the volume of sample applied to the pad, to prevent overfilling the pad and to allow determination of the final sample volume applied. From the known sample volume and amount of analyte, the concentration of analyte in the sample can be accurately calculated in reaction components, trapping agents, matrix configuration, and analyte tested can be made.

10 Claims, 4 Drawing Sheets

CONTROLLED-VOLUME ASSAY APPARATUS

Field of the Invention

The present invention relates to a method and apparatus for use in determining the concentration of a selected sample analyte, and more particularly, to a method and apparatus for applying a known volume of sample fluid to a dry reaction pad.

Background of The Invention

Assays for detecting the presence and levels of a variety of analytes in body fluid samples are known. Such assays are often designed for simplicity of use so that they can be reliably conducted in a doctor's office or other clinical setting where personnel may have little training in clinical assay procedure or in interpreting assay results. Typically, such assays involve a one-step assay procedure, or employ automated or semi-automated procedures, with the assay reading being determined from a reaction end-point.

One type of diagnostic assay format which is generally amenable to simple, one-step assays is an absorptive-pad device, containing a pad or matrix designed to absorb a sample volume, and to produce an analyte-dependent chemical reaction which can be detected on the pad's surface. Examples of absorptive-pad assay devices and methods include U.S. Pat. Nos. 3,983,005, 4,069,017, 4,144,306 and 4,447,575.

Although some assays are designed for qualitative yes/no determinations, more typically it is desired to quantitate the concentration of a particular analyte. For example, an accurate determination of blood cholesterol or triglycerides may be important in evaluating the patient risk for a number of lipid-related diseases, such as coronary artery diseases, or for evaluating the lowering of these blood analytes during the course of dietary or other treatment.

A number of factors have heretofore limited the accuracy of assays which are based on a conventional reaction matrix or pad format. One limitation is the variable amount of detectable reaction product formed in the presence of a given amount of analyte, due to variations in the stability of the reagents in the pad, variations in temperature and other reaction conditions, as well as the presence of variable amounts of interfering compounds in the analyte-containing sample.

These sources of variability have been largely eliminated in a three-pad self-corrected assay system and method in which analyte concentration is determined from a standard curve, and corrected for intereference based on the measured signal product readings from the three pads. The assay system is described in co-owned U.S. patent application for "Self-Corrected Assay Method and System", Ser. No. 238,775, filed Aug. 30, 1988. Another source of inaccuracy in determining analyte concentration by conventional reaction-pad assays stems from variations in sample volume to a pad. In particular, if an absorbent reaction pad is allowed to take up a liquid sample by surface wetting, it will tend to overfill, i.e., continue to fill even after complete wetting of the pad has occurred. The overfilling produces a surface film on the pad which may alter the reflectance or absorption characteristics of the pad, and thus skew the surface reading used to determine total analyte-dependent product formed in the reaction. The greater volume of sample in the pad will also increase uncertainty in the final analyte concentration (amount/volume) determination.

This problem can be partially solved by applying a known, preselected volume of sample to a dry reaction pad, for example, via a micropepette. This approach is somewhat laborious, however, and is also unsuitable in a multi-pad assay, such as mentioned above, in which sample is preferably applied simultaneously to the several pads. Also, to the extent that different reaction pads may have different absorption volumes, a preselected sample volume designed to fill one pad may overfill one.

SUMMARY OF THE INVENTION

It is one general object of the invention to provide a dry-pad assay method and apparatus which substantially ovecomes or solves the above-noted problems associated with applying a known volume of sample fluid to a dry reaction pad.

It is a more specific object of the invention to provide such method and apparatus for delivering a known volume of sample fluid to an absorbent reaction pad without overfilling the pad.

Another object of the invention is to achieve known volume delivery to several absorbent reaction pads simultaneously.

The invention includes, in one aspect, a diagnostic apparatus for use in connection with determining the concentration of a selected analyte in a body-fluid sample. The apparatus includes a wettable absorbent reaction pad which is effective to produce a detectable reaction product when the sample is applied to the pad, and structure for initiating and discontinuing delivery of a body fluid sample to a surface region of the pad, for sample distribution throughout an expanse of the pad.

The extent to which the pad's expanse has been wetted is monitored by a detector. A controller in the apparatus is operatively connected to the delivery structure, and responsive to the detector, for discontinuing delivery of fluid sample when the pad is wetted to a given extent, and preferably no later than when the pad is completely wetted, as monitored by the detector.

The delivery structure in the apparatus may operate to shift the pad relatively toward and away from the sample transfer position, to transfer sample from the reservoir to the pad. Alternatively, the delivery structure may include a spray mechanism for spraying sample onto the pad region.

The detector in the apparatus preferably includes a light source for directing a beam of light against the expanse of the pad, and an optical detector for detecting the intensity of the beam of light which is reflected from the pad.

In this embodiment, the controller is operative to calculate the rate of change of reflected light intensity received from the pad expanse at the optical detector, as sample is delivered to the pad. The controller places the delivery structure in its discontinuing mode no later than when a substantial reduction in the rate of change of reflected light intensity is detected.

The controller is also operative to calculate the volume of body fluid delivered to the pad, based on the change of reflected light intensity received from the pad expanse at the optical detector, as sample is delivered to the pad. Further, where the detectable product reaction produced in the pad causes a product-dependent reduction in reflected light intensity received at the optical detector, the controller is operative to calculate the amount of analyte contained in the pad, based on the measured change in reflected light intensity received at the optical detector after sample delivery to the pad, and to calculate the concentration of analyte based on the calculated amount of analyte in the pad, and the volume of sample fluid delivered to the pad.

In one embodiment of the invention designed for automated or semi-automated operation, the absorbent pad is part of a sample-delivery device which includes a sample dispenser having a sample reservoir, and a sample-transfer surface for transferring sample in the reservoir to the pad's surface region. The pad is carried on a support in the device, for movement therewith toward and away from a sample-delivery position at which the transfer surface is in contact with the pad's surface region. A resilient member may be interposed between the pad support and the dispenser, to bias the pad support away from the delivery position.

The apparatus further includes a measuring instrument having a holder for releasably supporting the sample-delivery device. The delivery structure, which is also part of the instrument, includes structure operatively connected to the holder for shifting the dispenser and pad support relatively toward and away from their delivery position, with the device supported in the holder. The detector and control mechanism in the apparatus are also part of the instrument.

In another aspect, the invention includes a sample-delivery device of the type just described. The device preferably includes a plurality of analyte-reaction pads mounted on the support, with the sample dispenser being adapted to deliver sample to each of the pads simultaneously, and at substantially the same sample-delivery rate.

When designed for use in a self-corrected assay of the type mentioned above, the device has at least three pads—a first designed for determination of total analyte contained in the delivered sample, a second designed for determination of total analyte plus a known amount of reference compound, and a third designed for determination of a different amount of a reference amount, which may be a background level of reference compound, when fluid sample is delivered to each of the pads.

Also forming part of the invention is a method useful in connection with determining the concentration of a selected analyte in a body-fluid sample. The method includes the steps of providing a wettable absorbent reaction pad, delivering a body fluid sample to a region of the pad for distribution throughout a defined expanse of the pad, detecting and monitoring the extent to which the expanse has been wetted, and in response to such detecting and monitoring step, automatically discontinuing the delivery of the body fluid sample to the pad.

The method of the present invention is useful for determining a variety of analytes, such as blood cholesterol and triglycerides.

Further objects, features and advantages of the present invention will become apparent from the following detailed description of the invention, when read in conjunction with the accompanying drawings.

DETAILED DESCRIPTION OF THE INVENTION

Figure 6:
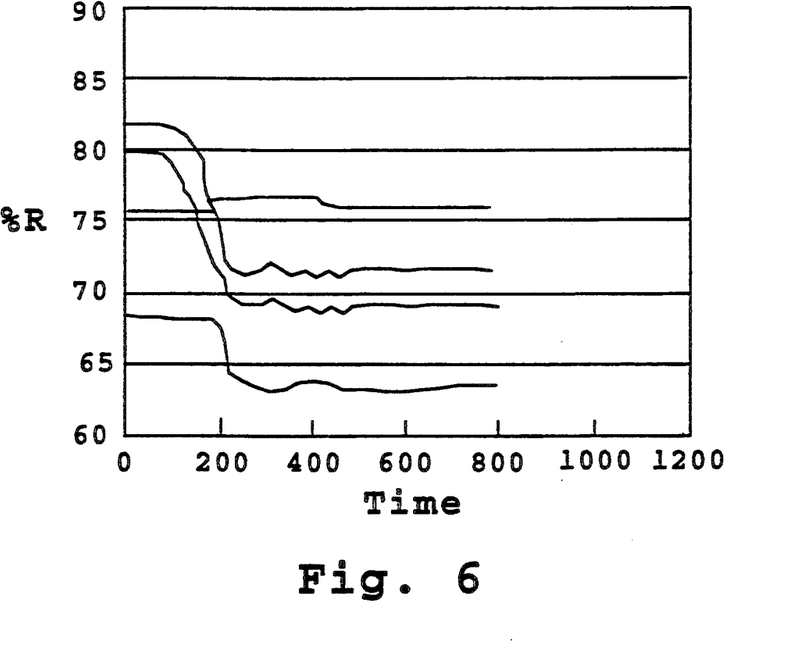
FIG. 6 plots the change in reflectance R as a function of time t during the period of sample fluid delivery into and through a reaction pad in the sample-delivery device of FIG. 1.
Figures 7A, 7B:
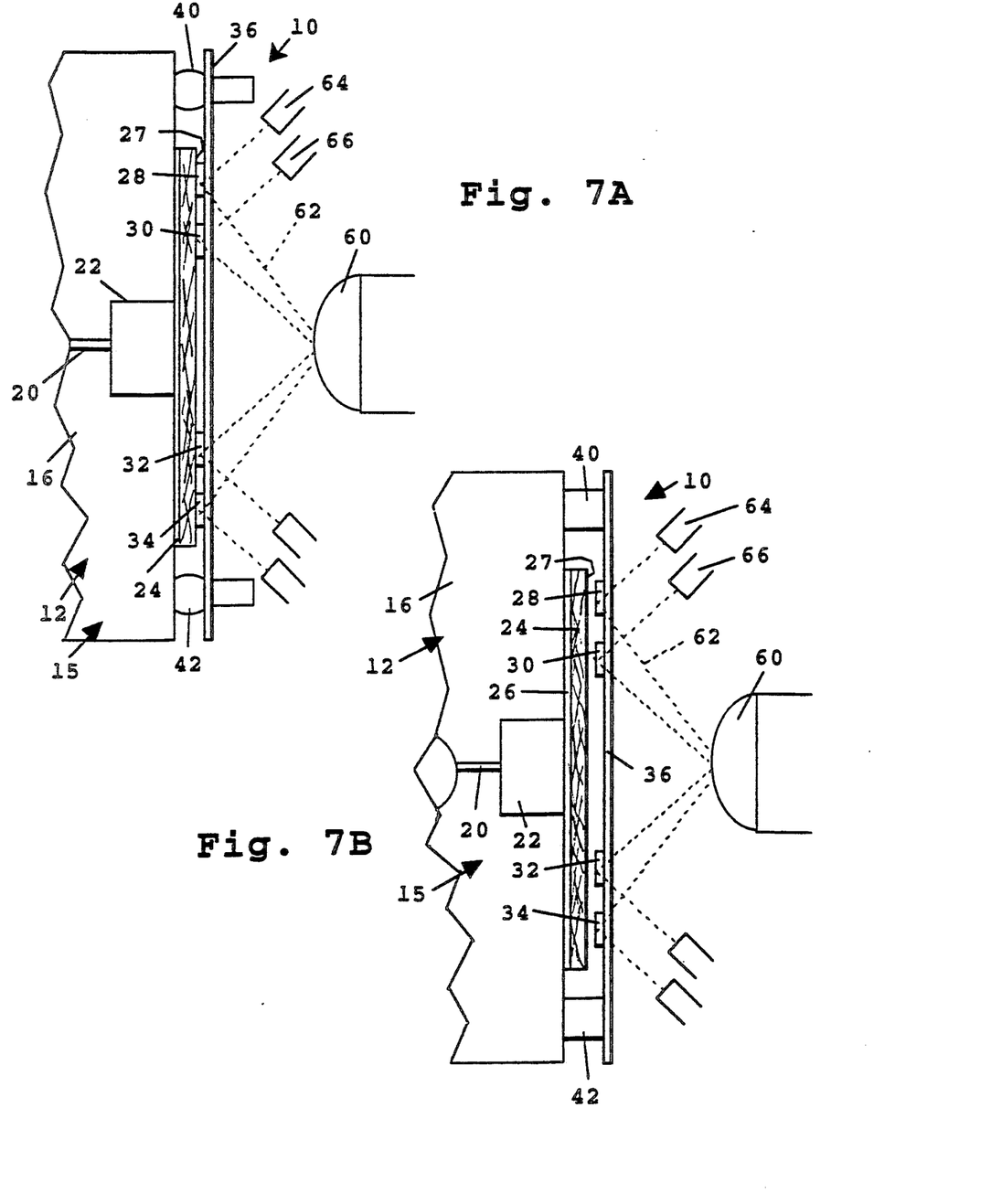
FIGS. 7A and 7B are plan views of the sample-delivery device of FIG. 1 in sample-delivery and non-delivery conditions, respectively, shown with part of the diagnostic apparatus for determining analyte concentration according to the invention.
Figure 8:
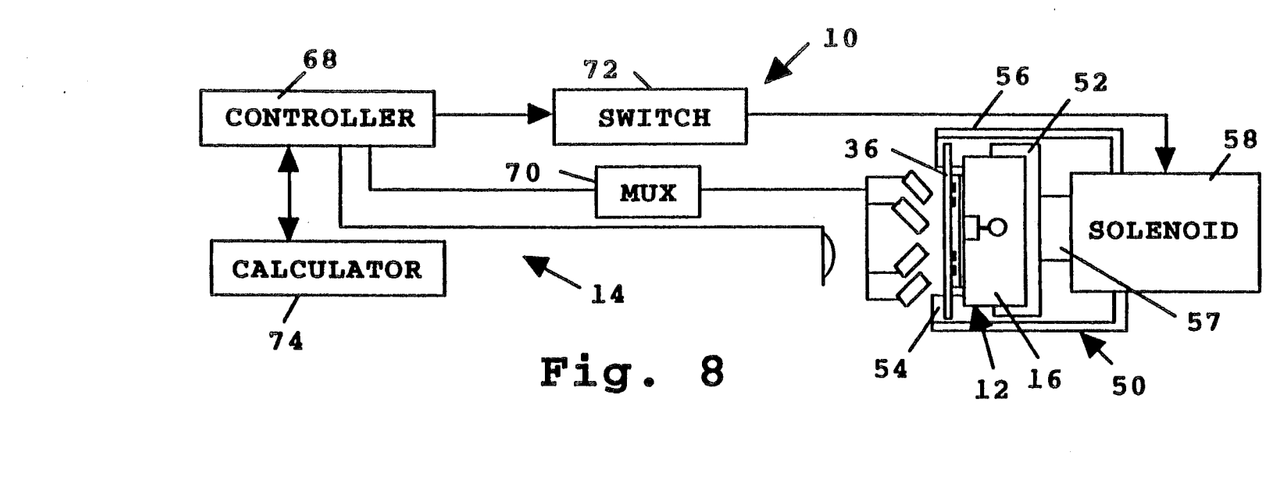
FIG. 8 is a schematic diagram of components of the apparatus of the invention.

FIGS. 1-8 ilustrate one preferred embodiment of the diagnostic apparatus of the invention, which is indicated generally at 10 in FIG. 8. The apparatus includes a sample-delivery device, which is seen generally at 12 in FIGS. 1-4 and 5-8, and a diagnostic instrument 14 whose components are seen in FIG. 8.

Figure 3:
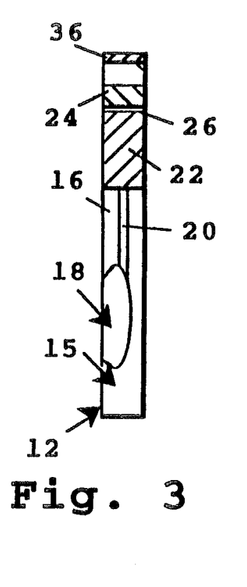
FIG. 3 is a sectional view taken along line 3—3 in FIG. 1.

With reference first to FIGS. 1-4, sample-delivery device 12 includes a sample dispenser 15 composed of a plate 16 which defines a well 18 dimensioned and sized to receive a quantity, such as 25 $\mu$l, of a fluid sample such as blood. A capillary conduit 20 formed in the plate is provided at the base of the well for conveying the blood sample to an absorbent filter 22, which is supported in an upper notched region of the plate, as seen. The upper surface of filter 22, which is flush with the upper edge of the plate in the figures, is covered by a microporous membrane 26. This membrane is in contact with an absorbent strip 24 which is attached to and extends along an interior portion of the plate's upper edge. As seen in FIG. 3, the filter, strip, and membrane all have about the same width dimension as plate 16, typically between 1-5 mm.

The sample volume supplied to the well 18 is calculated to substantially fill, but not overload, the delivery filter and strip. The fluid transferred to the delivery filter and strip, in accordance with this invention, is intended then to be delivered to one or more analyte-reagent or reaction pads, such as pad 28, in a controlled or predetermined amount, as will be described below.

Filter 22 and strip 24 are both preferably formed of a fibrous matrix filter material designed to draw aqueous fluid by surface wetting. A variety of fibrous materials, such as are used in fibrous-mat filters, including cellulose, cellulose acetate, and glass fibrous matrices, are suitable materials for the strip and sample pad. The fibers may be crosslinked, if desired, by chemical crosslinking, heat fusion, or the like. Also suitable are porous substrates, such as scintered glass, fused polymer beads, and the like whose wettability and dimension of interstices are such as to promote movement of an aqueous medium into the matrix by surface wetting. The pad preferably has a lower fiber density that the strip, giving greater fluid flow rate through the pad than through the strip.

One exemplary filter is a glass fiber filter having a packing density of about 0.2 gm/cm$^3$, side dimensions of between about 3 mm, and a thickness of about 125 $\mu$. The pad is dimensioned to absorb a defined volume of sample fluid, typically about 3-25 $\mu$l, and preferably between about 10-15 $\mu$l.

One exemplary strip is a glass fiber filter strip having a packing density of about 0.5 gm/cm$^3$, a length of about 3 cm, a width of about 3 mm, and a thickness of about 125 $\mu$. The pad is dimensioned to absorb a defined volume of sample fluid, typically about 3-25 $\mu$l, and preferably about 10 $\mu$l.

Membrane 26 attached to the lower surface of strip 24 is designed to filter out blood cells and other particulate matter present in the fluid sample. Where the device is used for assaying total cholesterol or other lipid components which may be associated with large lipoprotein bodies in the blood, the membrane pore sizes are selected to filter out blood cells, but allow allow passage of these lipid bodies through the membrane into strip 24. One preferred membrane is a polymemebrane membrane available from Nuclepore (Livermore, CA) and having a 1 micron pore size.

In a typical operation, a blood fluid sample is applied to the well and from here is drawn by capillarity through conduit 20 into filter 22. As the sample migrates through the filter and strip, the fibrous network material making up the filter retards the movement of particulate matter, including blood cells, acting to partially remove blood cells before the sample reaches membrane 26, thus reducing clogging effects at the membrane.

The well, filter, microporous membrane, and strip in the dispenser are also referred to herein collectively as a reservoir adapted to hold a quantity of sample fluid. The upper surface f the strip forms a sample-transfer surface 27 for delivering sample from the reservoir to the reaction pads.

Figure 1:
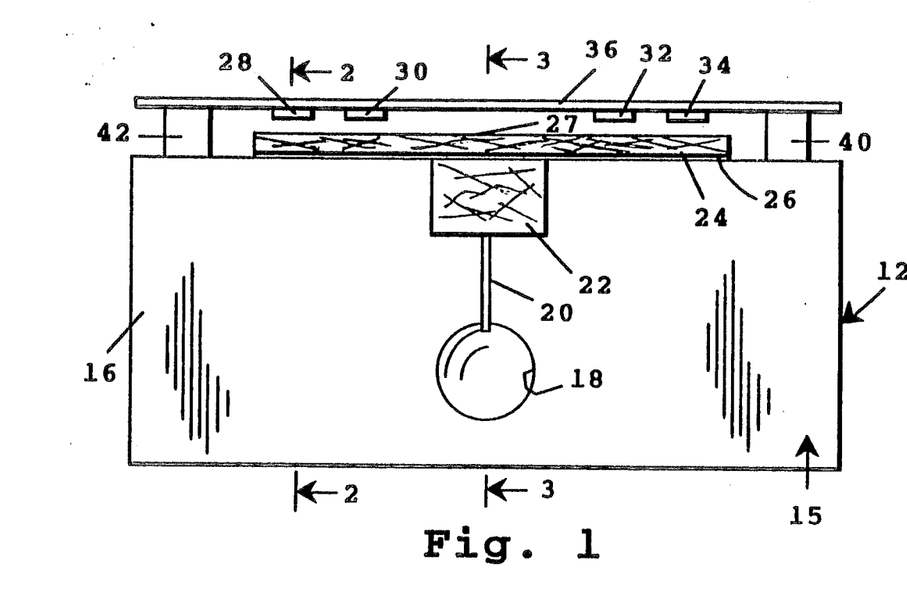
FIG. 1 is a plan view of a sample-delivery device for use in a diagnostic apparatus, all constructed according to the invention.
Figure 2:
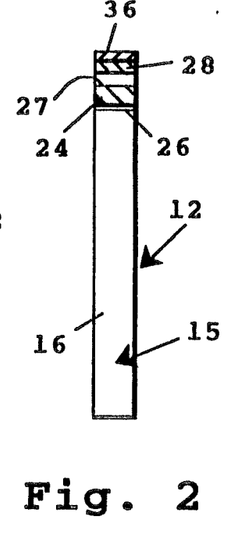
FIG. 2 is a sectional view taken along line 2—2 of FIG. 1.
Figure 4:
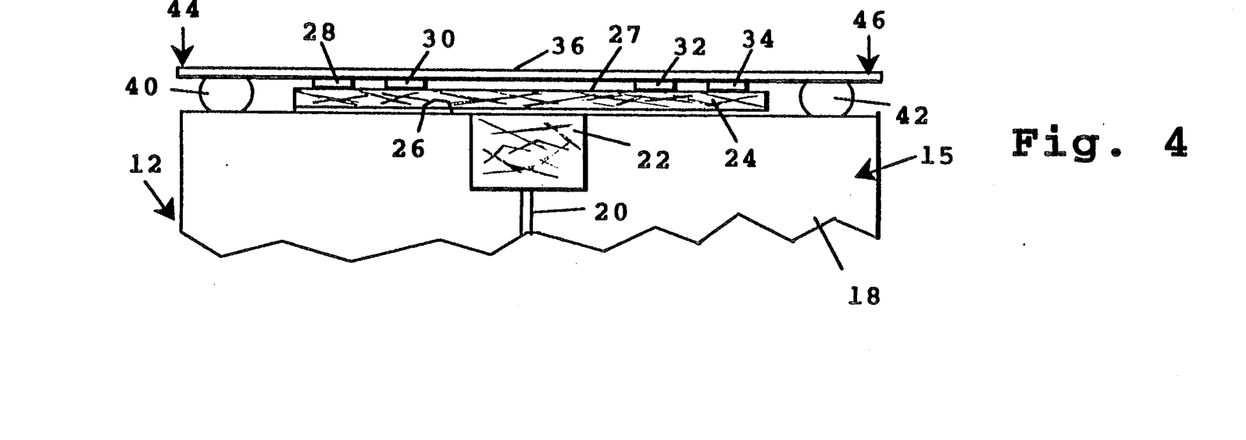
FIG. 4 is a plan view similar to FIG. 1, but showing the sample-delivery device in a sample-delivery position.
Figure 5:
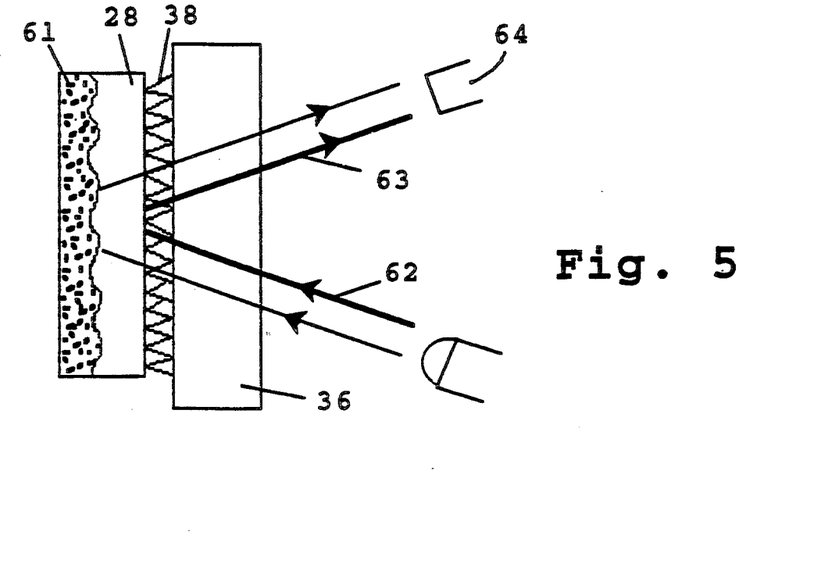
FIG. 5 is an enlarged side view of a reaction pad in the sample-delivery device, and an optical beam and sensor used for monitoring the change in reflectance at the back surface of the pad due to sample fluid flow into and through the reaction pad.

With continued reference to FIGS. 1-4, the reaction pads in the dispenser, which include the four pads 28, 30, 32, and 34, are carried on a transparent support 36 which is substantially co-extensive with the upper edge of plate 16, as seen in FIG. 1. With reference to FIG. 5, each pad is attached to the support by a transparent or translucent adhesive material 38. The four pads are positioned on the support for contact with transfer surface 27 in the dispenser, when the support is moved to a sample-delivery position (FIG. 4) at which the pads are in contact with the sample-transfer surface.

Each reaction pad contains analyte-dependent reagents adapted to produce an analyte-dependent change in the pad which can be detected optically, either visually or by a detector, in a known manner. The nature of the reagents for exemplary analyte assays is given below. Desirably, the reaction pads are porous, fused polymer substrate membranes having a thickness, after complete penetration of the fluid, of about 125 $\mu$ and side dimensions of about 3 mm. The absorption volume of each pad, in the embodiment described herein, is preferably between about 0.5-2 $\mu$l.

The support is mounted on the dispenser plate by a pair of resilient members, such as elastomeric blocks 40, 42. The blocks act to bias the pads in a non-delivery position at which the pads are spaced apart from the dispenser's sample-transfer surface, with a spacing typically of between about 0.5 to 1.0 mm.

The support, together with the associated reaction pads, is adapted to be shifted relative to the dispenser toward and away from a sample-delivery position at which transfer surface 27 in the dispenser is in contact with a surface region region of each pad —here the confronting lower surface of each pad in the figure—to initiate delivery of a body-fluid sample from the dispenser simultaneously to each pad.

To bring the pads into contact with the transfer surface, a plunger, such as a solenoid operated plunger described below, is provided and is operable to shift support 36 relative to the dispenser, by application of a force in the direction of arrows 44, 46 in FIG. 4, to move the pads to their sample-transfer positions. The plunger, which is part of the diagnostic instrument described below, is operable to hold the pads simultaneously at their sample-transfer position as long as desired, thereby to delivery a body fluid sample to the lower surface regions of the pads.

A relatively uniform force is exerted between the dispenser and reaction pads, in part due to the effect of the resilient blocks 40, 42, which become compressed during a sample-transfer operation, as seen in FIG. 7A. Optionally, a pair of resilient strips (not shown) may be placed between the upper edge of plate 16 and strip 24, on either side of filter 22, to further equalize the forces between the sample-transfer surface and each pad.

It should be noted that the sample transfer surface contacts each delivery pad at a predetermined surface region of each pad, which may be substantially less than the entire surface area of that pad. More generally, each pad has a surface region to which the fluid sample is delivered from transfer surface 27, and a defined expanse which is wetted during sample delivery. In the present embodiment, and as illustrated in FIG. 5, the surface region is the outer surface of the pad, and the expanse includes the thickness of the pad, through which sample fluid migrates, as indicated, from the zone of contact, during sample transfer to the surface region of sample application.

The material of each pad is effective to distribute the sample delivered to the region throughout the defined expanse at a given fluid-flow rate. That is, when a pad in the device is placed in a position of sample delivery, sample will migrate into and through the expanse of the pad at a rate which causes the pad to become completely wetted over a given sample-transfer time. Typically, in the embodiment described herein, a pad becomes completely wetted within a sample-transfer period of about 1-3 seconds.

The above-described sample-delivery device is preferably supplied for use as a disposable cartridge which is releasably inserted into the diagnostic instrument of the invention, for use in performing a single assay involving multiple pads, as described below, or more than one assays, for example, where the different pads are designed to measure different analytes.

Turning now to FIG. 8, the diagnostic instrument of the invention includes a sample holder 50 which receives the sample-delivery device releasably. The holder provides a plunger 52 designed to engage and support plate 16 in the device, and a pair of arms 54, 56 which are designed to engage and support opposite sides of support 36 in the device, as shown. The plunger is connected to the piston 57 of a solenoid 58, for movement therewith between a delivery position, at which the device is placed in a sample-transfer position, and a non-delivery position at which the device is in its normal spaced-apart configuration shown in FIG. 1.

As indicated above, the solenoid is operable to initiate sample delivery in the device, by movement to its delivery position, and to hold the device at the sample-delivery position (FIG. 7A) for a controlled period of time, after which sample delivery is discontinued (FIG. 7B) by solenoid movement to the non-delivery position. The solenoid, piston, and plunger are also referred to herein as shifting means for shifting the sample-transfer device toward and away from its sample-delivery position, and more generally, as means for initiating delivery and for discontinuing delivery of a sample to a surface region of a reaction pad.

According to an important aspect of the invention, instrument 14 further provides means for automatically controlling and determining when the desired amount of fluid sample has been delivered to the surface region of the reaction pads. To that end, the instrument (see FIGS. 7A, 7B and 8) includes a light source 60 which produces directed light beams, such as beam 62, which are directed at an angle against each reaction pad, with the sample-transfer device in holder 50.

For each pad, a light detector, such as detectors 64, 66 associated with pads 28, 30, respectively, in FIGS. 7A and 7B, is provided for monitoring the extent to which the expanse of the pad is wetted during delivery of the sample to the surface region of the pad. The light source and four detectors, which are contained in a light-tight housing which also contains holder 50, are also referred to herein as detector means for monitoring the extent to which the expanse of a reaction pad is wetted.

As will be appreciated, during sample transfer, as liquid sample migrates into and through the expanse of the pad, the reflectivity of the surface of the pad will decrease, due to the greater translucency of the pad, which is typically white and relatively reflective in its dry condition. FIG. 5 shows in enlarged scale the monitoring of a pad during sample transfer. Here beam 62 from the light source is directed through transparent support 36 and the adhesive material 38 against the surface of pad 28. As the pad is wetted by the migration of liquid 61 through the pad, the intensity of the reflectance beam 63 measured by detector 64 decreases, until the pad becomes completely wetted.

FIG. 6 shows typical plots of reflectance R measured in three pads during sample transfer, where each pad has a total absorption volume, for complete wetting of about 0.75 $\mu$l. The abscissa is a time scale, in hundredths of a seconds. Sample transfer is initiated at time t=0. All three pads show a sharp decrease in reflectance, over an approximately 2 second time period, after which reflectance plateaus, indicating complete wetting of the pad. As seen, each pad wetted completely at about the same rate.

In monitoring the change in reflectance from a pad surface, the amount of change can be determined and calculated so that when it reaches a predetermined value or predetermined differential value, based on previously generated data, it can be automatically determined that a desired amount of fluid sample has been delivered to the reagent pad. Then delivery can be discontinued, by retracting the solenoid to its non-delivery position.

The changes in reflectance measured by the detectors are monitored by a microprocessor controller 68 or control means which is operatively connected to the detectors through a multiplexer 70. The multiplexer operates conventionally to sample the signal outputs of the four detectors rapidly and sequentially, and input the signal outputs into the controller. As noted above, it has been determined that complete wetting of a 0.75 $\mu$l volume pad requires about 2 seconds. Thus, it has been determined that reflectance measurements every 100 milliseconds will provide sufficient data (20 data points) and monitoring to terminate delivery close enough to the optimum 0.75 $\mu$l without substantially under-delivering or over-delivering specimen.

The controller is suitably programmed to respond to a given change of reflectance or absolute reflectance value, and is preferably set to operate a switch 72 in the control means for switching the solenoid to its delivery position for a period of time which is no more than that required to effect wetting of any pad to the selected extent as determined by the associated detector, and then to switch the solenoid to its non-delivery position, to terminate sample transfer to the pads.

The control means desirably includes calculating means, such as a calculator 74, for calculating the rate of change of reflected light intensity received from the pad expanse at the optical detector, as sample is delivered to the pads. This calculation can be done conventionally, using, for example, a digital differentiator. Here switching to the non-delivery condition can be set to occur when the differential of the reflectance curve of any pad being monitored first reverses direction. The design of such a control means can be carried out readily according to well known solid-state design principles.

Preferably, the calculator is also designed to calculate the volume of liquid delivered to the pad, based on the change in reflected light intensity as monitored by the associated light detector. The volume calculation, in one embodiment, is made by determining the slope of the reflectance curve at the termination of sample-delivery to the pad, and correlating this slope with a predetermined table of values of slope vs. percent volume fill for a particular size pad.

In the embodiment shown, the detector means is also used to measure the change in reflectance in the associated pad due to the production of a colored reaction product in the pad, as analyte is utilized in forming the reaction product, after pad wetting occurs. As can be appreciated, when the light beam of the light source has a wavelength at or near the absorption maximum of the colored reaction product, the reflectance from the pad will decrease gradually with continued product of reaction product, until a new (second) reflectance-curve plateau is reached at the end point of the reaction. The total amount of analyte can then be calculated from the difference in reflectance at the first plateau (just after pad wetting) and at the second plateau (at the product end point). Alternatively, the amount of analyte can be calculated from reaction kinetics, based on the rate of change of reflectance observed after pad wetting. Microprocessor designs for performing such calculations are well known.

Based on the calculated volume of sample applied to a pad, and the amount of analyte contained in the volume, as determined by an analyte-dependent chemical reaction in the pad, the concentration of analyte in the sample can then be determined by the calculator.

Figure 9:
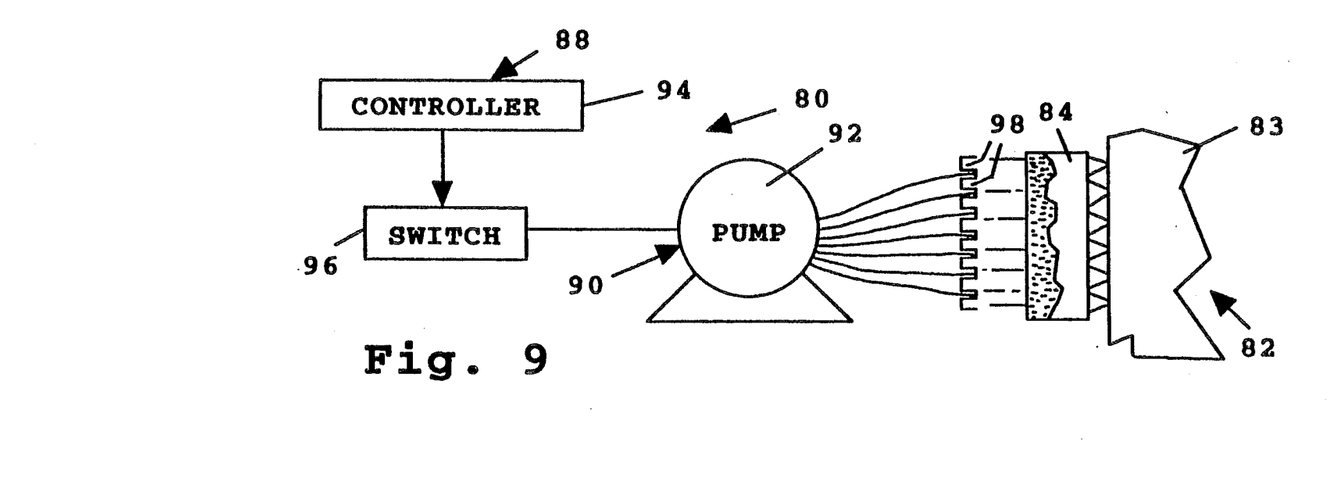
FIG. 9 is a partly schematic view of portions of an apparatus constructed according to further embodiment of the invention in which sample fluid is delivered to a reaction pad by spraying.

In the embodiment of FIGS. 1 to 8, the delivery of the fluid sample results from the physical contact of a delivery surface and the confronting surface of one or more reaction pads. As shown by FIG. 9, such delivery may alternatively be accomplished by a suitable sample spray delivery means by which fluid is sprayed onto one or more reaction pads in the apparatus. In such an apparatus, it is unnecessary to provide means, such as the resilient members in the sample-delivery device, and the shifting means in the diagnostic instrument, and other related components, for effecting transfer and delivery of the sample.

As such, the diagnostic apparatus of FIG. 9, indicated generally at 80, comprises a sample-delivery device, shown fragmentarily at 82, which is composed of a transparent support 83 and one or more reaction pads, such as pad 84. The attachment of the pads to the support by adhesive is as described above, and the wetting and formation of reaction product in the pad are monitored by suitable detectors means (not shown), as described above.

The sample-delivery device is supported in a suitable holder (not shown) in a diagnostic instrument 88 in the apparatus, which is like above-described instrument 14, except that the sample-transfer means in the instrument comprises a spray mechanism 90, or spray means, for spraying sample onto each of the reaction pads in the sample-transfer device. The spray mechanism includes a pump 92 which is under the control of a microprocessor controller 94 via a suitable switch 96.

The pump causes suitable spray head or nozzles 98 in the mechanism to spray sample against the surface region of the pad or reaction pads, such as pad 84, until the detector system determines that the pad expanse has been sufficiently wetted, following which the pump 92 is switched to its non-delivery condition.

The method of the invention which is performed by the diagnostic apparatus can be appreciated from the foregoing description of the apparatus. Briefly, a body fluid, a body-fluid sample, such as a blood sample, is delivered to a surface region of a wettable reaction pad, for distribution throughout a defined pad expanse. As the pad is wetted during sample delivery, the extent to which the expanse of the pad is wetted is detected and monitored. In response to this detecting and monitoring, the apparatus functions to automatically discontinue the delivery of the sample to the pad, at or before complete wetting of the pad occurs.

In one sample-transfer procedure, the fluid delivery step includes first adding the sample to a sample-delivery device dispenser having a reservoir for holding the sample and a sample-transfer surface for transferring sample in the reservoir to the pad surface region when the transfer surface is in contact with the pad region. The device is then shifted to a position at which the sample-delivery transfer surface of the dispenser is in contact with said pad region.

In a second sample-transfer procedure, the sample is added to an apparatus containing a dispenser having a spray mechanism for spraying sample onto the pad surface region, and a controller for activating the spray device.

The apparatus and method may be employed in connection with determining the concentration of a variety of different fluid analytes, and in a variety of analyte formats, as illustrated below.

The apparatus and method described with respect to FIGS. 1–8 are designed particularly for determination of blood analytes, where the blood sample is applied to the sample-dispenser well, filtered of particulate matter in its passage through the filter, strip, and microporous membrane, and the filtered serum or plasma sample then delivered to the reaction pads.

The reaction reagents in the reaction pad(s) may include an analyte-specific enzyme, and additional enzymic and/or other reagents for converting the product of the analyte-specific enzyme to a detectable, typically colored reaction product.

For example, in an assay for total serum cholesterol, the reaction pad(s) contains cholesterol esterase, cholesterol oxidase, a peroxidase, and a substrate reagent which is converted by the peroxidase in the presence of $H_2O_2$ to said detectable reaction product.

As another example, use in determing triglycerides in a blood-fluid sample, the reaction pad(s) contains lipase, a source of ATP, glycerol kinase, and glycerol-phosphate oxidase, for generating $H_2Op_2$, and the above components for generating a detectable reaction product in the presence of $H_2O_2$.

The apparatus and method of the invention are advantageous for use in connection with the three pad assay system and method described in co-owned U.S. patent application for "Self-Corrected Assay Method and System", Ser. No. 238,775, filed Aug. 30, 1985. Briefly, this system employs three separate reaction pads, such as pads 28, 30, and 32, in device 12, to allow determination of analyte concentration, based on a standard curve determination, with correction for background interference.

The present invention provides the additional advantage in this system that sample fluid is applied simultaneously to each of the three pads, and in known-volume amounts to each of the three pads, thus providing more accurate determinations of reaction product concentrations on which the corrected analyte concentration value is based.

From the foregoing, it will be appreciated how various objects and features of the invention are met. The apparatus provides an automated or semi-automated method for determining analyte concentrations in an applied sample. The method is easily performed, requiring only sample addition to a sample dispenser. By monitoring and controlling the volume applied to a reaction pad, the invention prevents overfilling, and thus eliminates inaccuracies in analyte determination due to surface liquid-film effects and to underestimation of volume. At the same time, where underfilling occurs, the invention provides an accurate measure of sample volume, for determining sample concentration.

Although the invention has been described with reference to exemplary and preferred embodiments and configurations, it will be apparent to those skilled in the art that various changes and modification may be made without departing from the invention.

It is claimed:

1. A diagnostic apparatus for use in determining the concentration of a selected analyte in a body-fluid sample, comprising
   sample dispenser having (i) a support, (ii) a well defined in the support for receiving such sample, (iii) a fibrous filter matrix, (iv) capillary means for drawing sample fluid from said well into the matrix, and (v) an absorbent strip on said support having a central region in fluid contact with said matrix for distributing ample fluid from the matrix by capillary flow to sample-delivery sites in opposite end regions of the strip, a test plate carrying a plurality of wettable, absorbent pads, each having an exposed outer surface region and a defined expanse, said plurality of pads containing reagent means effective to produce a detectable analyte-dependent reaction product for detection of a selected analyte, when sample fluid is transferred from said sample-delivery sites to said plurality of pads, and means mounting said plate on said dispenser, said mounting means being adjacent to and spaced from said plurality of pads, for movement toward and away from a sample-delivery position at which substantially the entire outer exposed surface regions of said plurality of pads are in contact with the sample-delivery sites, for simultaneous transfer of substantially the same volume of sample fluid from each of said delivery sites to each of said pads in the support with fluid movement at a substantially uniform flow rate in a direction normal to the pad outer surface regions throughout the entire expanse of each of said pads, whereby said pads are filled uniformly to a selected volume when said pads are held in contact with said sample-delivery sites for a selected period of time, and control means operatively connected to said shifting means for placing said support at its sample-delivery position for such sample-delivery time.

2. The apparatus of claim 1, wherein each of said plurality of pads is formed of a porous polymer membrane having a thickness, after complete penetration of said fluid, of between about 100–150 microns.

3. The apparatus of claim 1, for use in determination of total cholesterol in a blood-fluid sample, wherein said reagent means in at least one of said plurality of pads includes cholesterol esterase, cholesterol oxidase, a peroxidase, and a substrate reagent which is converted by the peroxidase in the presence of H2O2 to said detectable reaction product.

4. The apparatus of claim 1, for use in determination of triglycerides in a blood-fluid sample, wherein said reagent means in at least one of said plurality of pads includes lipase, a source of ATP, glycerol kinase, and glycerol-phosphate oxidase.

5. The apparatus of claim 1, which further includes detector means for monitoring the extent to which the expanse of one pad of said plurality of pads has been wetted, and wherein said control means is operatively connected to said detector means, for detecting the time required for substantially complete wetting of the pad.

6. The apparatus of claim 5, wherein said detector means is operative to substantially simultaneously detect the extent to which the expanse of each of said pads is wetted during delivery of the sample to the surface regions.

7. The apparatus of claim 5, wherein said detector means includes a light source for directing a beam of light against the expanse of the pad, and an optical detector for detecting the intensity of the beam of light which is reflected from the pad.

8. The apparatus of claim 7, wherein said control means includes calculating means for calculating the rat of change of reflected light intensity received from the pad expanse at the optical detector, as sample is delivered to the pad, and means for discontinuing transfer of sample no later than the time at which a substantial reduction in the rate of change of reflected light intensity is detected.

9. The apparatus of claim 8, wherein said calculating means is designed to calculate the volume of body fluid delivered to the pad, based on the change of reflected light intensity received from the pad expanse at the optical detector, as sample is delivered to the pad.

10. The apparatus of claim 9, wherein the detectable product reaction produced in the pad when an analyte-containing fluid sample is absorbed into the pad produces a product-dependent reduction in reflected light intensity received from the pad expanse at the optical detector, and said calculating means is designed to calculate the amount of analyte contained in the pad, based on the measured change in reflected light intensity received at the optical detector after sample has been delivered to the pad, and to calculate concentration of analyte based on the calculated amount of analyte in the pad, and the volume of sample fluid delivered to the pad.

* * * * *